United States Patent
Kopperschmidt

(10) Patent No.: US 9,452,252 B2
(45) Date of Patent: Sep. 27, 2016

(54) METHOD AND DEVICE FOR MONITORING A VASCULAR ACCESS AND EXTRACORPOREAL BLOOD TREATMENT DEVICE COMPRISING A DEVICE FOR MONITORING VASCULAR ACCESS

(76) Inventor: Pascal Kopperschmidt, Dittelbrunn (DE)

( * ) Notice: Subject to any disclaimer, the term of this patent is extended or adjusted under 35 U.S.C. 154(b) by 379 days.

(21) Appl. No.: 12/933,466

(22) PCT Filed: Mar. 24, 2009

(86) PCT No.: PCT/EP2009/002129
§ 371 (c)(1),
(2), (4) Date: Sep. 20, 2010

(87) PCT Pub. No.: WO2009/118145
PCT Pub. Date: Oct. 1, 2009

(65) Prior Publication Data
US 2011/0034814 A1   Feb. 10, 2011

(30) Foreign Application Priority Data
Mar. 27, 2008   (DE) .................. 10 2008 015 832

(51) Int. Cl.
*A61M 1/14* (2006.01)
*A61B 5/021* (2006.01)
*A61M 1/36* (2006.01)

(52) U.S. Cl.
CPC ......... *A61M 1/3653* (2013.01); *A61M 1/3656* (2014.02); *A61M 1/3639* (2013.01); *A61M 2205/15* (2013.01); *A61M 2205/18* (2013.01); *A61M 2205/3344* (2013.01)

(58) Field of Classification Search
CPC .................. A61M 1/3639; A61M 2001/3656; A61M 2205/15; A61M 5/16854; A61M 5/16859; A61M 5/172; A61M 2039/1005; A61M 2205/14; A61M 2205/3331; A61M 2205/3344; A61M 1/3656; A61M 1/3653; A61M 2001/3653; A61M 2205/18; A61M 2205/50; A61M 2205/70; G05B 13/0275; G05B 9/02; G05B 13/00; G05B 13/0265; G05B 13/027; G05B 13/028; G05B 13/0285; G05B 13/029; G05B 13/04; G05B 13/041; G05B 21/00; G05B 23/00
USPC ...................... 604/4.01, 5.01, 6.09, 6.1, 6.11
See application file for complete search history.

(56) References Cited

U.S. PATENT DOCUMENTS 4,979,940 A * 12/1990 Bobo et al. .................. 604/503
5,535,246 A *  7/1996 Beech .......................... 375/285

(Continued)

FOREIGN PATENT DOCUMENTS

| DE | 10115991 C1 | 4/2002 |
| DE | 102006032815 A1 | 1/2008 |
| WO | 97/10013 | 3/1997 |

OTHER PUBLICATIONS

Singh, Aarti. "Adaptive Noise Cancellation." Dept. of Electronics & Communication, Netaji Subhas Institute of Technology, 2008. http://www.cs.cmu.edu/~aarti/pubs/ANC.pdf#. Accessed Jul. 3, 2013.*

(Continued)

*Primary Examiner* — Adam Marcetich
(74) *Attorney, Agent, or Firm* — Kenyon & Kenyon LLP

(57) ABSTRACT

The invention relates to a method and a device for monitoring a vascular access during an extracorporeal blood treatment. The method and the device according to the invention are based on the monitoring of the difference between the venous pressure measured by a venous pressure sensor and the arterial pressure measured by an arterial pressure sensor (in the extracorporeal blood circuit. According to the method and the device according to the invention, a test function describing disturbances in the extracorporeal blood circuit is determined. Said test function is used to determine a noise-free differential pressure from the measured venous and arterial pressure, said differential pressure being evaluated in an arithmetic and evaluation unit to identify a defective vascular access.

18 Claims, 3 Drawing Sheets

(56) References Cited

U.S. PATENT DOCUMENTS

| | | | | |
|---|---|---|---|---|
| 5,906,589 | A * | 5/1999 | Gordon et al. | 604/65 |
| 6,083,187 | A * | 7/2000 | Nakayama et al. | 604/6.01 |
| 6,090,048 | A * | 7/2000 | Hertz et al. | 600/485 |
| 6,221,040 | B1 * | 4/2001 | Kleinekofort | 604/65 |
| 6,290,654 | B1 * | 9/2001 | Karakasoglu | 600/529 |
| 6,745,630 | B2 | 6/2004 | Gross | |
| 2001/0007930 | A1 | 7/2001 | Kleinekofort | |
| 2002/0174721 | A1 * | 11/2002 | Gross | 73/592 |
| 2003/0021389 | A1 * | 1/2003 | Hirai et al. | 379/3 |
| 2003/0136181 | A1 * | 7/2003 | Balschat | A61M 1/16 73/40.5 R |
| 2004/0030664 | A1 * | 2/2004 | Kotoulas et al. | 706/22 |
| 2004/0185804 | A1 * | 9/2004 | Kanamori et al. | 455/114.2 |
| 2005/0212589 | A1 * | 9/2005 | Batruni | 327/552 |
| 2005/0234361 | A1 * | 10/2005 | Holland | 600/510 |
| 2008/0013747 | A1 * | 1/2008 | Tran | 381/67 |
| 2008/0108930 | A1 * | 5/2008 | Weitzel et al. | 604/5.04 |
| 2009/0088683 | A1 * | 4/2009 | Roger | A61M 1/3653 604/65 |
| 2009/0270713 | A1 * | 10/2009 | Kimura et al. | 600/411 |
| 2009/0292236 | A1 | 11/2009 | Kleinekofort | |

OTHER PUBLICATIONS

Widrow, Bernard et al. "Adaptive Noise Cancelling: Principles and Applications." Proceedings of the IEEE, vol. 63, No. 12, Dec. 1975. http://labsegn.di.unimi.it/classici/Widrow_1975.pdf# accessed Jul. 3, 2013.*

International Search Report, PCT/EP2009/002129, mailed Aug. 10, 2009.

* cited by examiner

METHOD AND DEVICE FOR MONITORING A VASCULAR ACCESS AND EXTRACORPOREAL BLOOD TREATMENT DEVICE COMPRISING A DEVICE FOR MONITORING VASCULAR ACCESS

CROSS REFERENCE TO RELATED APPLICATIONS

This is a 371 national phase application of PCT/EP2009/002129 filed Mar. 24, 2009, claiming priority to German Patent Application No. 10 2008 015 832.1 filed Mar. 27, 2008.

FIELD OF INVENTION

The invention relates to a method of monitoring a vascular access during extra-corporeal blood treatment, and in particular during a chronic blood cleansing therapy such as haemodialysis, haemofiltration or haemodiafiltration, and to an arrangement for monitoring a vascular access for an extra-corporeal blood-treating apparatus in particular for haemodialysis, haemofiltration or haemodiafiltration. As well as this, the invention also relates to an extra-corporeal blood-treating apparatus having an arrangement for monitoring the vascular access.

In known methods employed in chronic blood-cleansing therapy, such as haemodialysis, haemofiltration and haemodiafiltration, blood from a patient is conveyed through an extra-corporeal blood circuit. As an access to the patient's vascular system, use is made of arteriovenous fistulas, vascular implants or even various catheters. The connection between the patient and the extra-corporeal blood circuit is generally made by means of needles which pierce the fistula or the vascular implant.

If, during the blood treatment, the connection between the extra-corporeal blood circuit and the vascular system becomes detached or a blood leak occurs in the extra-corporeal circuit, the patient can be prevented from suffering a serious loss of blood only if the extra-corporeal flow of blood is stopped immediately. As a rule, extra-corporeal blood circuits are therefore equipped with protective systems which constantly monitor the arterial and venous pressures ($P_A$ and $P_V$) within the system and any ingress of air into the extra-corporeal circuit.

BACKGROUND OF THE INVENTION

There are known pressure-based protective systems situated on the apparatus side which respond quickly in the event of the connection between the patient and the arterial segment of the extra-corporeal circuit becoming detached. However, it is not always certain that the known pressure-based protective systems will respond in the event of the venous needle coming out of the vascular access. Also, in the event of a blood leak in the system of venous tubing, it may happen that the resulting fall in venous pressure is not sufficiently great to ensure that the protective systems will trip.

U.S. Pat. No. 6,221,040 B1 describes an arrangement for monitoring a vascular access with which the slipping-out of both the arterial needle and the venous needle can be detected more reliably. To monitor the vascular access, the pressures in both the arterial segment of the extra-corporeal blood circuit and its venous segment are monitored by means of pressure sensors. Values characteristic of the state of the vascular access are calculated from the arterial and venous pressures in a calculating unit and these are analysed in an analysing unit to allow a faulty vascular access to be detected. To enable the values characteristic of the state of the vascular access to be calculated, the sum and the difference of the venous and arterial pressures in the extra-corporeal circuit can be determined.

As well as the above method in which the pressure in the arterial and venous segments of the extra-corporeal blood circuit is monitored, there are also known monitoring arrangements which are based on the monitoring of pulses of pressure which propagate in the extra-corporeal circuit.

DE 101 15 991 C1 (US 2002/0174721 A1) describes a method for detecting stenoses in a hose line system during an extracorporeal blood treatment, wherein an oscillating pressure signal is generated in the hose line system and the oscillating pressure signal is measured. The frequency spectrum of the oscillating pressure signal is analysed for the purpose of detecting stenoses, it being concluded that there is a stenosis when there is a change in the frequency spectrum. For this purpose, a Fourier transform of the oscillating pressure signal in the venous branch of the extracorporeal circuit is carried out. The static part is extracted from the Fourier spectrum of the venous pressure signal, wherein the attenuation of at least one harmonic oscillation of the pressure signal is ascertained and it is concluded that there is a stenosis from the change in the attenuation.

SUMMARY OF THE INVENTION

An object underlying the invention is to specify a method of monitoring a vascular access during extra-corporeal blood treatment which calls for relatively little cost or complication as far as the equipment is concerned, to enable a faulty vascular access to be detected on both the arterial and the venous sides of the extra-corporeal blood circuit with great safety and reliability.

A further object of the invention is to provide an arrangement for the safe and reliable monitoring of the arterial and venous vascular access for an extra-corporeal blood-treating apparatus, which arrangement calls for relatively little cost or complication as far as the equipment is concerned.

It is also an object of the invention to provide an extra-corporeal blood-treating apparatus which enables the arterial and venous vascular access to be monitored with great safety and reliability and with relatively little cost or complication as far as the equipment is concerned.

The method according to the invention and the arrangement according to the invention are based on the monitoring of the difference between the venous pressure in the venous segment of the extra-corporeal blood circuit and the arterial pressure in its arterial segment, a difference which is also referred to below as the venous and arterial pressure differential. To measure the arterial and venous pressures, use may be made in the method according to the invention and the arrangement according to the invention of sensors which are already present in known pieces of blood-treating apparatus. The change on the apparatus side to enable the protective system according to the invention to be implemented can thus be confined to a modification of the control system of the apparatus.

The invention is based on the finding that the values measured for the venous and arterial pressures have interfering signals superimposed on them and these signals are a basic problem which makes it difficult for the pressure signals which are measured to be analysed safely and reliably solely on the basis of the pressure differential to allow a faulty vascular access to be detected. The pressure signals are modulated by, for example, the blood pump arranged in the extra-corporeal blood circuit, the ultrafiltration pump and valves or the like.

In the method according to the invention and the arrangement according to the invention, a test function is determined which defines the interference in the extra-corporeal blood circuit. Using the test function, a pressure differential which is freed from interference is determined from the venous and arterial pressures which are measured, and this pressure differential is analysed to allow a faulty vascular access to be detected.

Basically, it is advantageous for the test function which defines the interference in the extra-corporeal blood circuit to be determined even when it is only the venous pressure in the extra-corporeal blood circuit which is monitored to enable a faulty vascular access to be detected. What is of advantage however is for account to be taken of both the venous and also the arterial pressure because it is possible, by monitoring the vascular access on the basis of the pressure differential, for changes in the hydrostatic pressure in the extra-corporeal blood circuit which are attributable to changes in the position of the patient access to be compensated for.

The actual analysis of the pressure differential which has been freed from interference, to enable a faulty vascular access to be detected, may be linked to a vast variety of criteria. The only thing which is crucial to the invention is that what is analysed is a pressure differential which has been freed from interference by means of the test function.

The determination of the pressure differential which has been freed from interference may be performed by first removing the interference from the individual arterial and venous pressure signals before the pressure differential is formed. It is however also possible for the pressure differential to be formed first and for the pressure differential then to have the interference removed from it.

Hence, where there is mention in the claims of the determination of a test function which defines interference affecting the arterial and venous pressures, this is intended to include both the case of a "single" removal of interference with a test function after the pressure differential has been formed and the case of a "double" removal of interference with two test functions before the differential is formed. The cases which are possible are thus as follows.

The interference is removed from the venous pressure $P_V$ with a test function $\hat{P}_V$ and from the arterial pressure $P_A$ with a test function $\hat{P}_A$ and the differential is formed from the two signals from which the interference has been removed. Consequently, there are two test functions.

The test function $\hat{P}_V$ is determined from $P_V$ and the test function $\hat{P}_A$ is determined from $P_A$, $P_V - P_A$ then having the interference removed from it with $P_V - P_A$. This case is equivalent to the first case but there is now only one test function.

The differential $P_V - P_A$ of the venous and arterial pressures has the interference removed from it with the test function $$(\widehat{P_V - P_A}).$$

In a preferred embodiment, which is notable for the relatively small amount of cost and complication involved in the calculation of the individual variables, the arterial and venous pressures are not freed from interference before the differential is formed but the differential between the venous and arterial pressures is formed first, and only after the differential has been formed does the freeing from interference of the pressure differential formed previously take place with the test function. By avoiding any separate removal of interference from the operands prior to the forming of the differential, the amount of calculating work required can be kept relatively low.

The invention is based on the finding that the interference is essentially of a cyclic nature. The test function can therefore be generated from a linear combination of trigonometrical functions where the trigonometrical functions satisfy the requirements for orthogonality. A test function of this kind allows the pressure differential to have interference removed from it after the forming of the differential.

The test function which defines interference affecting the venous and arterial pressures which are measured is a function which defines the pressure differential which is measured in a given interval of time during the extra-corporeal blood treatment, it being assumed that the vascular access is in order in the interval of time concerned, i.e. that the pressure differential is defined only by the interference in the system. This can for example be ensured by the physician checking the vascular access to see that it is in order.

In a subsequent interval of time, the test function determined in the preceding interval of time is then used to free the pressure differential measured in the subsequent interval of time from interference. For the subsequent interval of time, the test function determined in the preceding interval of time is thus taken as an estimated function which defines interference affecting the venous and arterial pressure signals. This applies particularly when the successive intervals of time follow one another in direct succession. The invention therefore makes provision for the test function to be determined at a time which is as close as possible.

In a preferred embodiment, the test function is determined successively during the extra-corporeal blood treatment and is continuously optimised during the blood treatment.

In principle the test function can be determined with different algorithms familiar to the person skilled in the art. Preferably, the coefficients of the test function are determined by the least squares method, a method that is known to the person skilled in the art.

In the simplest case, a preferred embodiment of the invention makes provision for the pressure differential, having been freed from interference, to be compared with a preset limiting value, the conclusion that there is a faulty vascular access being drawn if the pressure differential is less than a preset limiting value. It is however equally possible for other criteria to be used for the analysis of the pressure differential which has been freed from interference, which criteria may also be combined with one another.

In what follows, the method according to the invention for monitoring a vascular access and also an apparatus for extra-corporeal blood treatment having an arrangement for monitoring a vascular access will be explained in detail by reference to the drawings and to an embodiment.

DETAILED DESCRIPTION OF THE DRAWINGS

Figure 1:
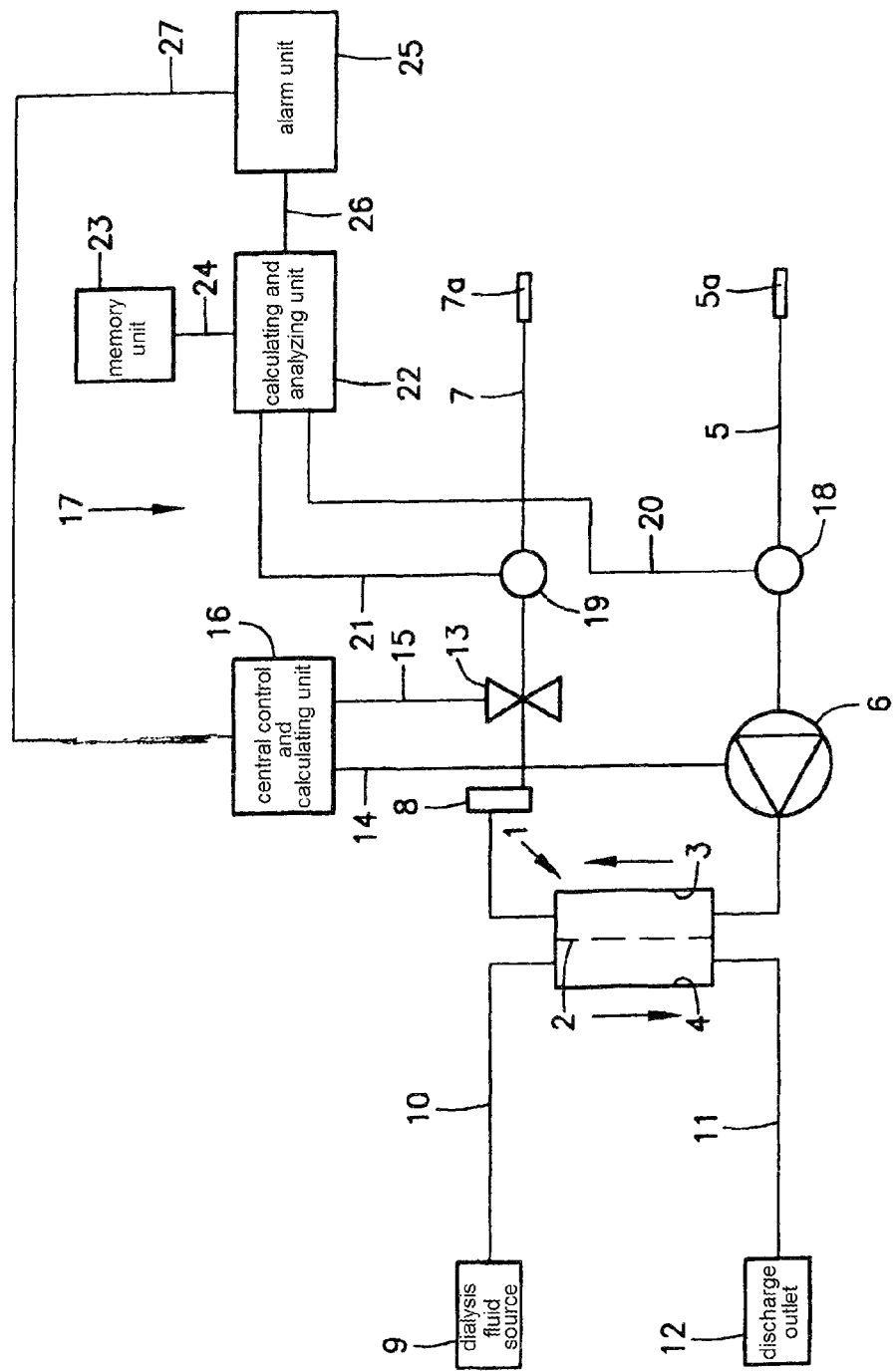
FIG. 1 is a highly simplified schematic representation of the main components of a haemodialysis apparatus together with the arrangement according to the invention for monitoring a vascular access.

FIG. 1 is a simplified schematic representation of a blood-treating apparatus having an arrangement for monitoring the arterial and venous vascular accesses, which apparatus has a blood-treating element which may be a dialyser, filter, adsorber, oxygenator or blood centrifuge. In the present embodiment the blood-treating apparatus is a dialysis apparatus which has a dialyser as a blood-treating element.

The monitoring arrangement may be an independent unit but may equally well be part of the dialysis apparatus. The monitoring arrangement is preferably part of the dialysis apparatus because there are individual components of the monitoring arrangement which are already present in the dialysis apparatus. The monitoring arrangement may, for example, make use of the pressure sensors which are present anyway in a dialysis apparatus and also the control and calculating unit of the dialysis apparatus.

The dialysis apparatus has a dialyser 1 which is divided by a semi-permeable membrane 2 into a blood chamber 3 and a dialysis-fluid chamber 4. Connected to the inlet of the blood chamber 3 is an arterial blood line 5 into which a peristaltic blood pump 6 is connected. Downstream of the blood chamber, a venous blood line 7 runs from the outlet of the blood chamber to the patient. Connected into the venous blood line 7 is a drip chamber 8. Connected to the ends of the arterial and venous blood lines 5, 7 are needles 5a, 7a which are inserted into the patient. The arterial and venous blood lines are part of a system of flexible tubing of a disposable form.

Fresh dialysis fluid is made available in a source 9 of dialysis fluid. From the source 9 of dialysis fluid, a dialysis-fluid infeed line 10 runs to the inlet of the dialysis-fluid chamber 4 of the dialyser, while a dialysis-fluid takeaway line 11 runs from the outlet of the dialysis-fluid chamber to a discharge outlet 12. The dialysis-fluid pump for feeding the dialysis fluid is not shown in FIG. 1.

To allow the flow of blood to be interrupted, there is provided on the venous blood line 7, downstream of the drip chamber 8, a shut-off clamp 13 which is electromagnetically actuated. The arterial blood pump 6 and the venous shut-off clamp 13 are operated by a central control and calculating unit 16 of the dialysis apparatus via control lines 14, 15.

The dialysis apparatus may also have other components such for example as a balancing means and an ultrafiltration means, but for the sake of greater clarity these have not been shown in FIG. 1.

The arrangement 17 for monitoring the vascular access has a measuring unit, which has a pressure sensor 18 monitoring the pressure in the arterial blood line 5 and a pressure sensor 19 monitoring the pressure in the venous blood line 7. The measured values from the pressure sensors 18, 19 are transmitted via data lines 20, 21 to a calculating and analysing unit 22 belonging to the monitoring arrangement 17, in which the measured values are analysed to allow a faulty vascular access to be detected. The calculating and analysing unit 22 of the monitoring arrangement 17 may also be part of the central control and calculating unit 16 of the dialysis apparatus. The interim results which occur in the course of calculation are stored in a memory unit 23 which is connected to the calculating and analysing unit 22 via a data line 24.

Connected to the calculating unit 22 of the monitoring arrangement 17 via a control line 26 is an alarm unit 25 which is connected via a further control line 27 to the central control and calculating unit 16 of the dialysis apparatus.

In what follows, the theoretical principles of the pressure monitoring process and the way in which the monitoring arrangement according to the invention operates will be explained in detail.

The venous pressure which is measured in the venous blood line 7 on the apparatus side is made up, when the blood pump 6 is turning, of the back pressure from the venous piercing needle 7a, the internal pressure at the fistula, and a hydrostatic pressure which is dependent on the geometrical difference in height between the venous pressure sensor 19 and the patient's heart and which changes if there is a vertical change in the position of the patient. The principal contribution to the venous pressure is made by the back pressure upstream of the venous needle 7a. The pressure signal from the venous pressure sensor 19 is generally not a steady-state signal but has cyclic interfering signals superimposed on it by the blood pump 6 and the ultrafiltration pump (not shown) and by hydraulic valves and other components (not shown) of the dialysis apparatus.

The internal pressure at the fistula, which makes only a small contribution to the venous pressure, is composed of the mean blood pressure and the rheological pressure drop downstream of the puncture which is caused by the generally venous vascular system. The contribution to the venous pressure measured on the apparatus side which is made by the internal pressure at the fistula is approximately 8 to 10% and varies between 15 and 35 mm Hg as a function of the nature of the patient access.

If there is a dislocation of the venous piercing needle, the venous pressure goes down by the contribution made by the internal pressure at the fistula. Some of the known monitoring systems however are not able to detect the reduction in the internal pressure at the fistula which is attributable to a faulty vascular access because the pressure does not normally drop below the lower limit which is monitored for the venous pressure. The invention however allows the reduction in the internal pressure at the fistula due to a faulty vascular access to be detected, by eliminating the interfering contributions to the venous pressure. The venous pressure which has been stabilised in this way retains its dynamic characteristics and can be used during the dialysis as a measured variable for monitoring the vascular access.

In the event of the venous needle becoming disconnected, the venous pressure which has been freed from the cyclic interference falls, while the arterial pressure measured on the apparatus side remains largely unchanged. Basically, there is therefore no need for the arterial pressure to be taken into account. However, there may be a change in the hydrostatic pressure due to changes in the patient's position. The invention therefore makes provision not only for the venous pressure to be monitored but also for the differential between the venous and arterial pressures to be monitored.

If the position of the puncture changes, if the patient raises his arm or stands up for example, the effect of a change in the hydrostatic pressure is compensated for by determining the pressure differential.

Because a changing arterial pressure generally results in a change in the cross-section of the part of the blood tubing which leads away from the blood pump, which latter is preferably peristaltic, the effective rate at which the blood is pumped goes down if there is a fall in arterial pressure and hence so too do the back pressures in the arterial and venous piercing needles 5a, 7a. A vertical change in the position of the patient therefore results in slightly different reactions at the arterial and venous points of measurement, which reactions are dependent on the absolute arterial pressure. These reactions can be allowed for in the case of the invention, as will be explained below.

During the extra-corporeal blood treatment, the measured values ($P_A$ and $P_V$) from the arterial and venous blood sensors 18, 19 of the measuring unit are continuously sensed, are averaged in the calculating and analysing unit 22 over a half-cycle of the blood pump 6 and are stored in the memory unit 23. Due to the different ways in which the arterial and venous pressure sensors 18, 19 are coupled to the system of blood tubing 5, 7, it may be necessary for the dynamic characteristics of the sensors to be adjusted. This is preferably done by low-pass filtering the pressure measured by the arterial pressure sensor 18, filtering which takes place in the calculating and analysing unit 22.

Figure 2:
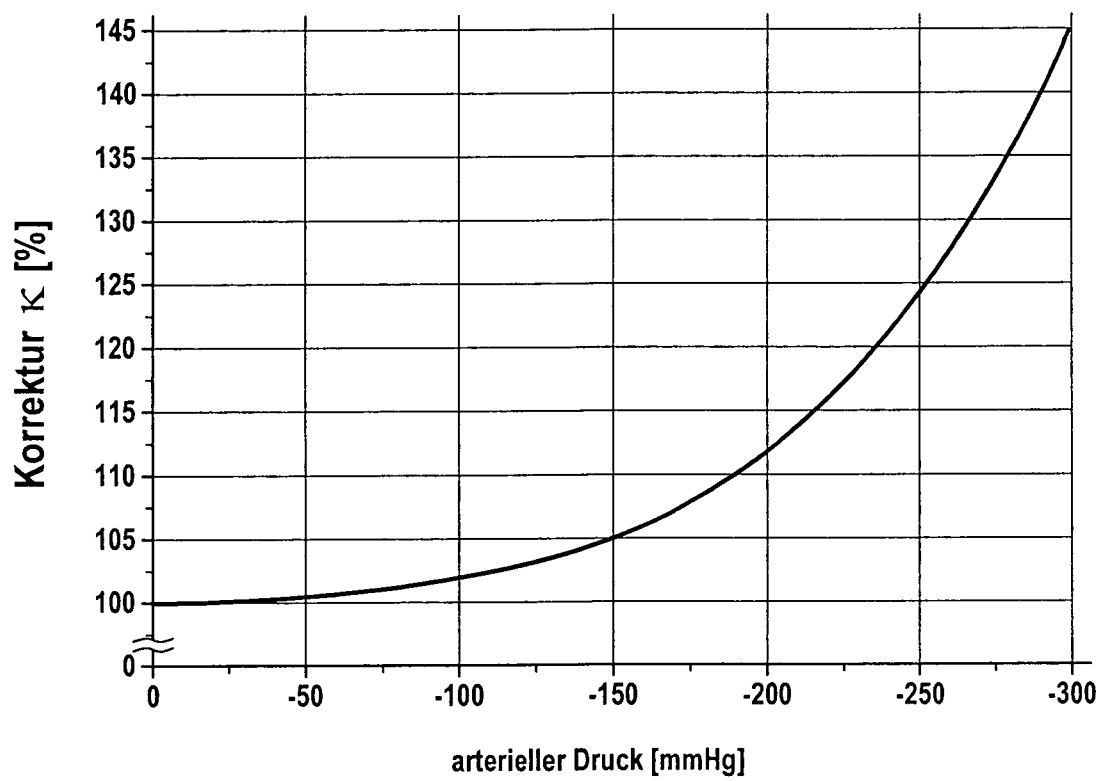
FIG. 2 shows a correcting factor for correcting the pressure differential as a function of the arterial pressure.

To apply compensation to the pressure signals as a result of the changes mentioned in the position of the patient which result in changes in the hydrostatic pressure at the points where pressure is measured, the calculating and analysing unit determines a correcting factor κ as a function of the arterial pressure $P_A$. FIG. 2 shows an example of a functional dependence of κ ($P_A$). Where $P_A$>0 there is generally no need for any correction, i.e. κ($P_A$) is usefully equal to 100% in this range.

To allow a faulty vascular access to be detected, the calculating and analysing unit 22 monitors the compensated pressure differential $P_{VA}(t)$ found from the venous and arterial pressures ($P_V(t)$ and $P_A(t)$), which is calculated from the following equation.

$$P_{VA}(t)=\kappa(P_A)\cdot[P_V(t)-P_A(t)] \quad (1)$$

This function can usefully be found at times $t=n\pi/\omega_{Qb}$, where n is the number of rotor heads or rollers which the blood pump 6 has and $\omega_{Qb}$ is the angular frequency of the blood pump. This being the case, the pump rotates through the same angle, and there is thus a constant amount of blood pumped, between each pair of points of measurement, regardless of the actual speed of pumping. In other words, the reaction time or speed of reaction then goes hand in hand with a given amount of blood which in each case is constant.

If there is a venous disconnection, the amount of blood which flows through the disconnected needle is thus independent of the pumping rate of the blood pump, and the monitoring criteria are therefore coupled to the blood flow.

The calculating and analysing unit 22 also continuously monitors the following test function during the extra-corporeal blood treatment.

$$\hat{P}_{VA}(t) = B_0 + \sum_{k=1}^{K}\sum_{n=1}^{N}[A_{nk}\sin(n\omega_k t) + B_{nk}\cos(n\omega_k t)] \quad (2)$$

The coefficients A and B in equation (2) determine the contributions made by the higher harmonics of order n of the cyclic interference k of frequency $\omega_\kappa$. The coefficients A and B are successively estimated during the extra-corporeal blood treatment by the least squares method. The estimate is optimised at each half-rotation of the blood pump. A forgetting factor determines the coupling between the estimate which is obtained at the time and the estimate which is already in the past.

In equation (2), the first summand $B_0$ gives the stable pressure differential freed from interference while the second summand gives the contribution made to the interference by all the cyclic contributors. Because the coefficients of the contributions change only slowly if the estimation is successful, an approximation of the conditions of pressure in the immediate future can be obtained by means of equation (2). The determination of the test function takes place as follows in the calculating and analysing unit 22.

The test function defines the pressure differential $P_{VA}(t)$ found from the venous and arterial pressures which are measured by the venous and arterial pressures pressure sensors 18, 19 within an interval of time during the blood treatment in which it can be assumed that there is a proper vascular access, when corrected by the correcting factor. Because the vascular access which exists in this interval of time is not faulty, the corrected pressure differential $P_{VA}(t)$ corresponds to the pressure $\hat{P}_{VA}(t)$ defined by the test function, this pressure comprising only the proportion of interference and the useful signal ($B_0$).

The test function $\hat{P}_{VA}(t)$ which is determined in the preset interval of time is taken as an estimated function for a subsequent interval of time in which a faulty vascular access is to be detected. A faulty vascular access is detected in the subsequent interval of time when certain criteria which are preset in the calculating and analysing unit are met when the compensated pressure differential and the estimated function (test function) are compared.

The determination of the test function by the least squares method is based on the following theoretical principles.

It is assumed that the interference constitutes a signal which is made up of a plurality of signal emitters of different frequencies. This signal is to be broken down into a series of harmonic functions. The breakdown is to include proportions of all the signal emitters. By means of the recursive least squares (RLS) method, an estimate is to be made of the Fourier coefficients and a successive optimisation of the coefficients is to be successfully performed.

Let p(t) be the physically measured output signal for the discrete sensing of time. The estimated function of the output signal is the sum of a harmonic breakdown d(t) given by:

$$d(t) = \sum_{k=0}^{K}\sum_{n=0}^{N}\left[\alpha_{n,k}\sin\left(2\pi n\frac{t}{T_k}\right) + \beta_{n,k}\cos\left(2\pi n\frac{t}{T_k}\right)\right] \quad (3)$$

The Fourier coefficients of the harmonic n and the signal emitter k are given by $\alpha_{n,k}$ and $\beta_{n,k}$. The corresponding cycle lengths are $T_k$. K is the number of signal emitters and N is the number of limited higher harmonics which is considered sufficient for the breakdown. By means of a suitable low-pass filter, the harmonics required for the estimate are limited by p(t).

With a knowledge of the cycle lengths of the signal emitters, the coefficients of the estimate d(t) are now determined, which means that the sum of the root-mean-square errors of the distance $|p(t)-d(t)|^2$ for a number of time-sensing instants t in the discrete interval of time [M–I,M] is minimised.

This is particularly true if allowance is made for a forgetting factor $0<\lambda<1$ which reduces the effect of the root-mean-square distances which are situated in the past in time.

$$\sum_{t'=t}^{t-M}\lambda^{t-t'}|p(t')-d(t')|^2 = \min \quad (4)$$

With a constant λ, there is consequently a reduction in the weight which a difference between p(t') and d(t') has when the extreme values are considered, as the time-span t–t' between the present and the time at which the point in time t' is situated in the past becomes increasingly long.

There are however also other mathematical methods of determining the test function which are familiar to the person skilled in the art.

The test function (estimated function) having been determined, the calculating and analysing unit 22 subtracts the approximation of the pressure conditions, which does not include the stable contribution, from the pressure differential $P_{VA}(t)$ which is measured:

$$PP_{VA}(t) = P_{VA}(t) - (\hat{P}_{VA}(t) - B_0) \tag{5}$$

The pressure differential $PP_{VA}(t)$ which is obtained is an observable whose dynamics are comparable to those of the measured variable $P_{VA}$ but which does not have any proportion of cyclic interference. This observable can also be freed from individual instabilities which are now, however, of a cyclic nature. A spike filter for example can be used for this purpose.

During the extra-corporeal blood treatment, the calculating and analysing unit 22 makes a continuous check on the following criterion.

$$[B_0 - PP_{VA}(t)] > Crit_0 \tag{6}$$

The above criterion is met as soon as a positive change by $Crit_0$ takes place in the interference-free pressure differential $PP_{VA}$ relative to the slowly varying stable contribution $B_0$. If this happens, the calculating and analysing unit 22 produces an alarm signal which the alarm unit 25 receives via the control line 26. The alarm unit 25 then emits an audio and/or visual alarm. The alarm unit also transmits a control signal, via the control line 27, to the control and calculating unit 16 of the dialysis apparatus, which then closes the venous shut-off clamp 13 and stops the blood pump 6, thus interrupting the blood treatment.

Figure 3:
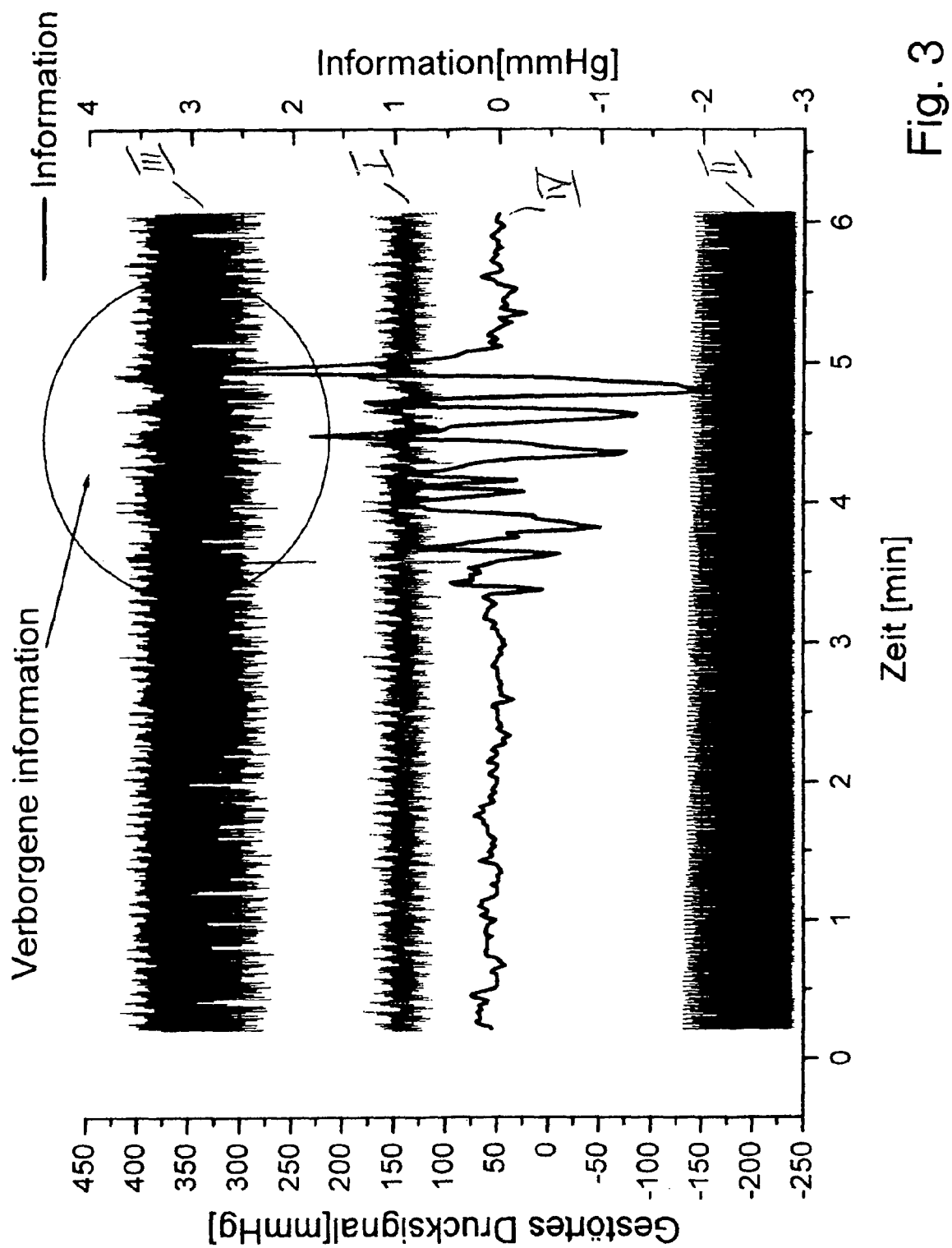
FIG. 3 shows the pressure signals which are subject to interference and which have been freed from interference, as a function of time.

To illustrate the method, FIG. 3 shows the pressure differential found from venous pressure and arterial pressure, which is subject to interference, as a function of time, the venous pressure $P_V$ and arterial pressure $P_A$ being measured by the venous and arterial pressure sensors 19, 18 and the pressure differential being calculated from the venous and arterial pressures in the calculating and analysing unit 22. The venous pressure signal which is measured by the venous pressure sensor 19 is identified in FIG. 3 by reference numeral I, while the arterial pressure signal measured by the arterial pressure sensor 18 is identified as II. The pressure differential is identified as III.

FIG. 3 also shows as a function of time the pressure differential which has been freed from interference, which is identified by reference numeral IV and which, to allow it to be shown clearly, is not shifted by $B_0$ as it is in equation (5) but reproduces the function $PP_{VA}(t) = P_{VA}(t) - \hat{P}_{VA}(t)$. For signal IV, the significant axis is the Y axis on the right. The pressure differential was obtained by comparing the signal for pressure differential which was measured with the test function (estimated function). If the signal for pressure differential which is measured is identical to the test function (estimated function) or differs only slightly from the signal for pressure differential which is measured, there is assumed to be a vascular access which is in order. If however there is a faulty vascular access, the signal for pressure differential which is measured is not identical to the test function (estimated function) and differs by a preset amount from the test function, which latter defines only the cyclic interference which exists when there is a proper vascular access. This becomes clear from a change in the pressure differential which has been freed from interference (signal IV). The interference which is shown in FIG. 3 corresponds in this case to handling operations which were carried out on the tubing system for test purposes.

The invention claimed is:

1. A method of monitoring a vascular access during extra-corporeal blood treatment in which blood flows from the vascular access via an arterial segment of an extra-corporeal blood circuit into a blood-treating element, and from the blood-treating element via a venous segment back into the vascular access, comprising the steps of:
   measuring a pressure in the venous and arterial segments of the extra-corporeal blood circuit in a first interval of time wherein there is a proper vascular access;
   determining a test function that defines interference affecting the measured arterial and venous pressures in the first interval of time, wherein the test function is an estimated function that defines interference affecting the arterial and venous pressures for a subsequent second interval of time;
   removing the interference from the individual arterial and venous pressures measured in the first interval of time;
   determining a first pressure differential that is freed from interference from the measured venous and arterial pressures in the first interval of time;
   measuring a pressure in the venous and arterial segments of the extra-corporeal blood circuit in the subsequent second interval of time;
   determining a second pressure differential from the measured venous and arterial pressures in the subsequent second interval of time;
   freeing the second pressure differential from interference by comparing the second pressure differential to the test function; and
   analyzing the second pressure differential that has been freed from interference to detect a faulty vascular access.

2. The method according to claim 1, further comprising: determining the test function successively during the extra-corporeal blood treatment.

3. The method according to claim 2, further comprising: determining the difference between the second pressure differential and the test function; and
   concluding that there is a faulty vascular access if the difference between the second pressure differential and the test function is more than a preset limiting value.

4. The method according to claim 3, wherein the test function is determined from a linear combination of trigonometrical functions.

5. The method according to claim 4, wherein the test function is defined by the following equation:

$$\hat{P}_{VA}(t) = B_0 + \sum_{k=1}^{K} \sum_{n=1}^{N} [A_{nk} \sin(n\omega_k t) + B_{nk} \cos(n\omega_k t)]$$

where the coefficients A and B determine the contributions made by the higher harmonics of order n of the cyclic interference k of frequency ωk.

6. The method according to claim 1, further comprising: determining the difference between the second pressure differential and the test function; and concluding that there is a faulty vascular access if the difference between the second pressure differential and the test function is more than a preset limiting value.

7. The method according to claim 1, wherein the test function is defined by the following equation:

$$\hat{P}_{VA}(t) = B_0 + \sum_{k=1}^{K} \sum_{n=1}^{N} [A_{nk}\sin(n\omega_k t) + B_{nk}\cos(n\omega_k t)]$$

where the coefficients A and B determine the contributions made by the higher harmonics of order n of the cyclic interference k of frequency ωk.

8. The method according to claim 1, wherein analyzing the second pressure differential that has been freed from interference to detect a faulty vascular access comprises:
detecting the faulty vascular access on a basis of a contribution of internal pressure at a fistula.

9. An arrangement for monitoring a vascular access for an extra-corporeal blood-treating apparatus for performing extra-corporeal blood treatment in which blood flows from the vascular access via an arterial segment of an extra-corporeal blood circuit into a blood-treating element, and from the blood-treating element via a venous segment back into the vascular access, said arrangement comprising:
a measuring unit configured to measure a first pressure in the venous and arterial segments of the extra-corporeal blood circuit in a first interval of time wherein there is a proper vascular access, and configured to measure a second pressure in the venous and arterial segments of the extra-corporeal blood circuit in a subsequent second interval of time; and
an analyzing unit for analyzing the measured first and second venous and arterial pressures to enable a faulty vascular access to be found, wherein the analyzing unit comprises:
a test function unit configured to determine a test function that defines interference affecting the measured first arterial and venous pressures in the first interval of time, wherein the test function is an estimated function that defines interference affecting the arterial and venous pressures for the subsequent second interval of time;
wherein the analyzing unit is configured to:
remove the interference from the individual first arterial and venous pressures measured in the first interval of time;
determine a first pressure differential that is freed from interference from the measured first venous and arterial pressures in the first interval of time;
determine a second pressure differential from the measured second venous and arterial pressures in the subsequent second interval of time;
free the second pressure differential from interference by comparing the second pressure differential to the test function; and
analyze the second pressure differential that has been freed from interference to detect a faulty vascular access.

10. The arrangement according to claim 9, wherein the analyzing unit is configured to determine the test function successively during the extra-corporeal blood treatment.

11. The arrangement according to claim 10, wherein the analyzing unit is configured to analyze the difference between the second pressure differential and the test function, such that the faulty vascular access is detected if the difference between the second pressure differential and the test function is more than a preset limiting value.

12. The arrangement according to claim 11, wherein the analyzing unit is configured such that the test function is determined from a linear combination of trigonometrical functions.

13. The arrangement according to claim 12, wherein the analyzing unit is configured such that the test function is defined by the following equation:

$$\hat{P}_{VA}(t) = B_0 + \sum_{k=1}^{K} \sum_{n=1}^{N} [A_{nk}\sin(n\omega_k t) + B_{nk}\cos(n\omega_k t)]$$

where the coefficients A and B determine the contributions made by the higher harmonics of order n of the cyclic interference k of frequency ωk.

14. An apparatus for extra-corporeal blood treatment having an arrangement for monitoring a vascular access according to claim 9.

15. The arrangement according to claim 9, wherein the analyzing unit is configured to analyze the difference between the second pressure differential and the test function, such that the faulty vascular access is detected if the difference between the second pressure differential and the test function is more than a preset limiting value.

16. The arrangement according to claim 9, wherein the analyzing unit is configured such that the test function is defined by the following equation:

$$\hat{P}_{VA}(t) = B_0 + \sum_{k=1}^{K} \sum_{n=1}^{N} [A_{nk}\sin(n\omega_k t) + B_{nk}\cos(n\omega_k t)]$$

where the coefficients A and B determine the contributions made by the higher harmonics of order n of the cyclic interference k of frequency ωk.

17. The arrangement according to claim 9, wherein the analyzing unit is so designed that the faulty vascular access is detected on a basis of a contribution of internal pressure at a fistula.

18. An apparatus for extra-corporeal blood treatment comprising:
a vascular access;
an arterial segment;
a venous segment;
a blood-treating element; and
an arrangement for monitoring the vascular access comprising:
a measuring unit configured to measure a first pressure in the venous and arterial segments in a first interval of time wherein there is a proper vascular access, and configured to measure a second pressure in the venous and arterial segments in a subsequent second interval of time; and
an analyzing unit for analyzing the measured first and second venous and arterial pressures to enable a faulty vascular access to be found, wherein the analyzing unit comprises:
a test function unit configured to determine a test function that defines interference affecting the measured first arterial and venous pressures in the first interval of time, wherein the test function is an estimated function that defines interference affecting the arterial and venous pressures for the subsequent second interval of time;

wherein said analyzing unit is configured to:
remove the interference from the individual first arterial and venous pressures measured in the first interval of time;
determine a first pressure differential that is freed from interference from the measured first venous and arterial pressures in the first interval of time;
determine a second pressure differential from the measured second venous and arterial pressures in the subsequent second interval of time;
free the second pressure differential from interference by comparing the second pressure differential to the test function; and
analyze the second pressure differential that has been freed from interference to detect a faulty vascular access.

* * * * *